(12) United States Patent
Byun et al.

(10) Patent No.: US 10,799,856 B2
(45) Date of Patent: Oct. 13, 2020

(54) FERRITE-BASED CATALYST, PREPARATION METHOD THEREFOR, AND METHOD FOR PREPARING BUTADIENE USING SAME

(71) Applicant: LG CHEM, LTD., Seoul (KR)

(72) Inventors: Young Chang Byun, Daejeon (KR); Ara Cho, Daejeon (KR); Jeong Seok Lee, Daejeon (KR); Mi Kyung Kim, Daejeon (KR); Daehyeon Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 52 days.

(21) Appl. No.: 16/082,181

(22) PCT Filed: Mar. 30, 2017

(86) PCT No.: PCT/KR2017/003504
§ 371 (c)(1),
(2) Date: Sep. 4, 2018

(87) PCT Pub. No.: WO2017/171441
PCT Pub. Date: Oct. 5, 2017

(65) Prior Publication Data
US 2019/0076836 A1    Mar. 14, 2019

(30) Foreign Application Priority Data

Mar. 30, 2016 (KR) .................. 10-2016-0038436
Jun. 17, 2016 (KR) .................. 10-2016-0075916

(51) Int. Cl.
*B01J 37/03* (2006.01)
*B01J 23/80* (2006.01)
(Continued)

(52) U.S. Cl.
CPC ............... *B01J 37/03* (2013.01); *B01J 21/04* (2013.01); *B01J 21/063* (2013.01); *B01J 21/066* (2013.01);
(Continued)

(58) Field of Classification Search
CPC . B01J 37/03; B01J 21/04; B01J 21/063; B01J 21/066; B01J 21/08; B01J 21/12;
(Continued)

(56) References Cited

U.S. PATENT DOCUMENTS 3,270,080 A * 8/1966 Christmann ......... B01J 27/1853
585/622
3,308,183 A * 3/1967 Laimonis .................. C07C 5/56
585/620
(Continued)

FOREIGN PATENT DOCUMENTS

KR     100847206 B1    7/2008
KR     100888143 B1    3/2009
(Continued)

OTHER PUBLICATIONS

Toledo, et al.: "Oxidative dehydrogenation of 1-butene over Zn—Al ferrites", XP055069766, Journal of Molecular Catalysis, Elsevier, vol. 125, No. 1, Oct. 1, 1997, pp. 53-62.
(Continued)

*Primary Examiner* — Patricia L. Hailey
*Assistant Examiner* — Michael Forrest
(74) *Attorney, Agent, or Firm* — Dentons US LLP

(57) ABSTRACT

The present specification provides a ferrite catalyst, a method for preparing the same and a method for preparing butadiene using the same.

17 Claims, 1 Drawing Sheet

(51) Int. Cl.
| | |
|---|---|
| C07C 5/333 | (2006.01) |
| C07C 11/167 | (2006.01) |
| B01J 37/08 | (2006.01) |
| B01J 37/00 | (2006.01) |
| B01J 35/10 | (2006.01) |
| B01J 37/04 | (2006.01) |
| B01J 37/02 | (2006.01) |
| B01J 23/00 | (2006.01) |
| B01J 35/08 | (2006.01) |
| C01G 49/00 | (2006.01) |
| B01J 35/02 | (2006.01) |
| B01J 21/04 | (2006.01) |
| B01J 21/06 | (2006.01) |
| B01J 21/08 | (2006.01) |
| B01J 21/12 | (2006.01) |
| B01J 23/887 | (2006.01) |

(52) U.S. Cl.
CPC .............. *B01J 21/08* (2013.01); *B01J 21/12* (2013.01); *B01J 23/005* (2013.01); *B01J 23/80* (2013.01); *B01J 35/023* (2013.01); *B01J 35/08* (2013.01); *B01J 35/1009* (2013.01); *B01J 35/1076* (2013.01); *B01J 37/0036* (2013.01); *B01J 37/0209* (2013.01); *B01J 37/0215* (2013.01); *B01J 37/031* (2013.01); *B01J 37/033* (2013.01); *B01J 37/038* (2013.01); *B01J 37/04* (2013.01); *B01J 37/08* (2013.01); *C01G 49/0063* (2013.01); *C07C 5/333* (2013.01); *C07C 11/167* (2013.01); *B01J 23/8876* (2013.01)

(58) Field of Classification Search
CPC ........ B01J 23/005; B01J 23/80; B01J 35/023; B01J 35/08; B01J 35/1009; B01J 35/1076; B01J 37/0036; B01J 37/0209; B01J 37/0215; B01J 37/031; B01J 37/033; B01J 37/038; B01J 37/04; B01J 37/08; C01G 49/0063; C07C 5/333; C07C 11/167

See application file for complete search history.

(56) References Cited

U.S. PATENT DOCUMENTS

| | | | |
|---|---|---|---|
| 3,849,545 A | * | 11/1974 | Miklas .................. B01J 23/80 |
| | | | 423/594.2 |
| 2010/0121123 A1 | * | 5/2010 | Chung ................. B01J 23/002 |
| | | | 585/629 |
| 2016/0326071 A1 | | 11/2016 | Kim et al. |

FOREIGN PATENT DOCUMENTS

| | | |
|---|---|---|
| KR | 1020120009687 A | 2/2012 |
| KR | 1020140082869 A | 7/2014 |
| KR | 1020150036205 A | 4/2015 |
| WO | 2015190801 A1 | 12/2015 |

OTHER PUBLICATIONS

Lee, et al.: "Preparation of ZnFe2O4 Catalysts by a Co-precipitation Method Using Aqueous Buffer Solution and Their Catalytic Activity for Oxidative Dehydrogenation of n-Butene to 1,3-Butadiene", XP055559658, Catalysis Letters, vol. 122, No. 3-4, Dec. 11, 2007, pp. 281-286.

* cited by examiner

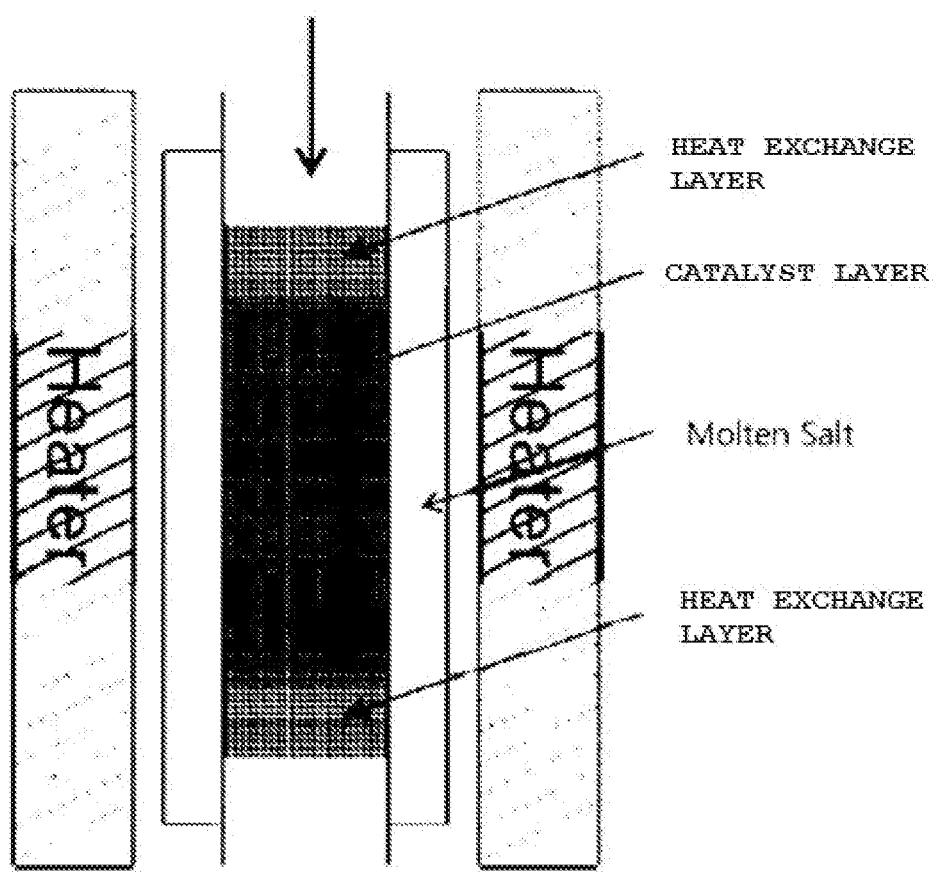

FERRITE-BASED CATALYST, PREPARATION METHOD THEREFOR, AND METHOD FOR PREPARING BUTADIENE USING SAME

TECHNICAL FIELD

This application is a National Stage Application of International Application No. PCT/KR2017/003504 filed on Mar. 30, 2017, and claims priority to and the benefits of Korean Patent Application No. 10-2016-0038436, filed with the Korean Intellectual Property Office on Mar. 30, 2016, and Korean Patent Application No. 10-2016-0075916, filed with the Korean Intellectual Property Office on Jun. 17, 2016, the entire contents of which are incorporated herein by reference.

The present application relates to a ferrite catalyst, a method for preparing the same, and a method for preparing butadiene using the same.

BACKGROUND ART

An oxidative dehydrogenation reaction of butene for preparing butadiene, for which demands have gradually increased in the petrochemistry market, is a reaction producing butadiene and water by the reaction of butene and oxygen, and is capable of lowering a reaction temperature as well as being thermodynamically advantageous since stable water is produced as a product.

An oxidative dehydrogenation reaction of normal-butene (1-butene, trans-2-butene, cis-2-butene) is a reaction producing butadiene and water by the reaction of normal-butene and oxygen. However, many side reactions such as a complete oxidation reaction are expected since oxygen is used as a reactant in the oxidative dehydrogenation reaction, and suppressing such side reactions as much as possible and developing catalysts having high selectivity is most important core technology. Catalysts used in an oxidative dehydrogenation reaction of butene known so far may include ferrite series catalysts, tin series catalysts, bismuth molybdate series catalysts and the like.

Among these, the ferrite catalyst has different activity as a catalyst depending on the type of metal occupying a divalent cation site of a spinel structure, and among these, zinc ferrite, magnesium ferrite and manganese ferrite are known to exhibit favorable activity for an oxidative dehydrogenation reaction of butene, and particularly, zinc ferrite has been reported to have higher butadiene selectivity compared to ferrite catalysts of other metals [F.-Y. Qiu, L.-T. Weng, E. Sham, P. Ruiz, B. Delmon, Appl. Catal., Vol. 51, page 235 (1989)].

Utilization of a zinc ferrite series catalyst in an oxidative dehydrogenation reaction of butene has been reported, and in order to increase reaction activity and lifetime of a zinc ferrite catalyst for an oxidative dehydrogenation reaction, pre-treatment and post-treatment such as treating the catalyst with additives may be performed, and butadiene is known to be obtained in a higher yield in the long term therethrough.

In preparing butadiene through oxidative dehydrogenation of butene using a ferrite series catalyst, the oxidative dehydrogenation reaction used to be performed under the condition of excessive steam of 10 times or more compared to butene amount, and this is due to the fact that steam is known to, as well as lowering a partial pressure of butene performing a role of lowering an explosion range, enhance stability of a reactor by removing reaction heat released during the oxidative dehydrogenation reaction, increase a conversion rate of butene and increase selectivity for butadiene by directly acting on the catalyst surface.

However, using 10 times or more of steam compared to butene amount has a problem in that, in addition to costs of the steam itself, heat energy corresponding to at least latent heat of water may be wasted when recuperating heat energy of reactants including steam and then condensing through compression/cooling at the back end of a reactor. Accordingly, when using steam in excess in a process of an oxidative dehydrogenation reaction of butene, steam itself costs much and heat energy loss is high, and in addition thereto, costs for treating excessive waste water incurs since a small amount of oxygenates produced during the oxidative dehydrogenation reaction of butene is included in condensed water, and as a result, economic feasibility of a process may not be secured.

Accordingly, development of catalysts capable of increasing conversion rate and yield of butadiene even under the condition of using less steam has been urgently required so as to increase economic feasibility of an oxidative dehydrogenation process of butene.

DISCLOSURE

Technical Problem

The present application is directed to providing a ferrite catalyst capable of obtaining butadiene in a high yield by increasing a conversion rate of butene and increasing butadiene selectivity while using a small amount of steam, a method for preparing the same, and a method for preparing butadiene through the same.

Technical Solution

One embodiment of the present application provides a method for preparing a ferrite catalyst including preparing an aqueous precursor solution including a metal precursor; mixing the aqueous precursor solution with a basic solution and coprecipitating the result; obtaining a solid sample through heat treatment after the coprecipitating; preparing slurry by mixing the solid sample in distilled water and grinding the result; loading the slurry into a carrier; and baking the slurry-loaded carrier, wherein the carrier has a pore structure, and the pore structure has, when employing, in a distance from a center to a surface of the carrier, the center as 0% and the surface as 100%, porosity of 10% to 50% in 0% to 50%.

Another embodiment of the present application provides a ferrite catalyst for preparing butadiene prepared using the method according to one embodiment of the present specification.

Still another embodiment of the present application provides a method for preparing butadiene using a ferrite catalyst including providing oxygen, nitrogen, butene and steam; an oxidative dehydrogenation reaction performed by the gas mixture continuously passing through a fixed bed of the catalyst layer prepared according to one embodiment of the present specification; and yielding butadiene.

Advantageous Effects

A ferrite catalyst according to one embodiment of the present application is capable of obtaining butadiene in a high yield while using a small amount of steam.

The ferrite catalyst according to one embodiment of the present application is capable of controlling activity per unit volume of the catalyst, and therefore, is capable of stably operating a reactor by lowering an inner temperature of the catalyst layer.

In addition, the ferrite catalyst according to one embodiment of the present application is capable of increasing process efficiency of the preparation method by reducing the generation of waste water.

DESCRIPTION OF DRAWINGS

FIG. 1 is a sectional diagram of a reactor used in an oxidative dehydrogenation reaction of butene according to one embodiment of the present specification.

MODE FOR DISCLOSURE

Hereinafter, the present specification will be described in more detail.

One embodiment of the present specification provides a method for preparing a ferrite catalyst including preparing an aqueous precursor solution including a metal precursor; mixing the aqueous precursor solution with a basic solution and coprecipitating the result; obtaining a solid sample through heat treatment after the coprecipitating; preparing slurry by mixing the solid sample in distilled water and grinding the result; loading the slurry into a carrier; and baking the slurry-loaded carrier, wherein the carrier has a pore structure, and the pore structure has, when employing, in a distance from a center to a surface of the carrier, the center as 0% and the surface as 100%, porosity of 10% to 50% in 0% to 50%.

Porosity means a portion occupied by pores in a fixed volume, and having porosity of 10% to 50% in 0% to 50% from the carrier center may mean pores being provided inside the carrier as well, and the slurry being sufficiently loaded into the pores inside the carrier as well.

A method of measuring the porosity is not particularly limited, and commonly usable techniques may be used. For example, water absorption may be used.

In addition, one embodiment of the present specification may provide a method for preparing a ferrite catalyst in which the metal precursor includes any one selected from the group consisting of a metal chloride precursor and a metal nitrate precursor.

According to one embodiment of the present specification, there may be provided a method for preparing a ferrite catalyst in which the metal nitrate precursor includes zinc nitrate ($Zn(NO_3)_2 \cdot 6H_2O$), iron nitrate ($Fe(NO_3)_3 \cdot 9H_2O$) and a nitrate salt additive, and the nitrate salt additive is any one or more selected from the group consisting of beryllium nitrate ($Be(NO_3)_2$), magnesium nitrate ($Mg(NO_3)_2 \cdot 6H_2O$), calcium nitrate ($Ca(NO_3)_2 \cdot 4H_2O$), strontium nitrate ($Sr(NO_3)_2 \cdot 4H_2O$), barium nitrate ($Br(NO_3)_2$), aluminum nitrate ($Al(NO_3)_3 \cdot 9H_2O$), chromium nitrate ($Cr(NO_3)_3 \cdot 9H_2O$), cobalt nitrate ($Co(NO_3)_2 \cdot 6H_2O$), manganese nitrate ($Mn(NO_3)_2 \cdot 6H_2O$), copper nitrate ($Cu(NO_3)_2 \cdot 6H_2O$), nickel nitrate ($Ni(NO_3)_2 \cdot 6H_2O$), lanthanum nitrate ($La(NO_3)_3 \cdot 6H_2O$), cerium nitrate ($Ce(NO_3)_3 \cdot 6H_2O$) and bismuth nitrate ($Bi(NO_3)_3 \cdot 5H_2O$).

According to one embodiment of the present specification, there may be provided a method for preparing a ferrite catalyst in which the metal chloride precursor includes zinc chloride ($ZnCl_2$), iron chloride ($FeCl_3 \cdot 6H_2O$) and a chloride additive, and the chloride additive is any one or more selected from the group consisting of beryllium chloride ($BeCl_2$), magnesium chloride ($MgCl_2 \cdot 6H_2O$), calcium chloride ($CaCl_2 \cdot 6H_2O$), strontium chloride ($SrCl_2 \cdot 6H_2O$), barium chloride ($BaCl_2 \cdot 2H_2O$), aluminum chloride ($AlCl_3 \cdot 6H_2O$), chromium chloride ($CrCl_3 \cdot 6H_2O$), cobalt chloride ($CoCl_2 \cdot 6H_2O$), manganese chloride ($MnCl_2 \cdot 4H_2O$), copper chloride ($CuCl_2 \cdot 2H_2O$), nickel chloride ($NiCl_2 \cdot 6H_2O$), lanthanum chloride ($LaCl_3 \cdot 7H_2O$), cerium chloride ($CeCl_3 \cdot 7H_2O$) and bismuth chloride ($BiCl_3 \cdot 5H_2O$).

When using the metal chloride precursor, a process of washing and filtering may be included after mixing the aqueous precursor solution including the metal chloride precursor with a basic solution and coprecipitating the result, however, when using the metal nitrate precursor, a process of washing and filtering may not be included depending on a basic solution type used, and a solid sample may be obtained with heat treatment only.

According to one embodiment of the present specification, in the mixing of the aqueous precursor solution with a basic solution and coprecipitating of the result, the basic solution may be any one selected from the group consisting of sodium hydroxide (NaOH), potassium hydroxide (KOH) and ammonium hydroxide ($NH_4OH$).

According to one embodiment of the present specification, the coprecipitating may be coprecipitating while mixing the aqueous precursor solution with the basic solution having a molar concentration of 1.5 to 12 at 10° C. to 40° C.

According to one embodiment of the present specification, in the obtaining of a solid sample through heat treating the coprecipitated solution, the coprecipitated solution is phase separated for a sufficient period of time so as for the precipitates to settle down, and after washing, the precipitated solid sample may be obtained through a vacuum filter and the like. In addition, the coprecipitated solution may have a pH of 5 to 10.

According to one embodiment of the present specification, washing and filtering may be additionally included prior to the heat treatment. This may vary depending on the basic solution type used in the coprecipitating. Although not particularly limited thereto, washing and filtering may be additionally included prior to the heat treatment when the basic solution is sodium hydroxide (NaOH) or potassium hydroxide (KOH).

According to one embodiment of the present specification, the ferrite catalyst includes a carrier and a baked solid sample, and the baked solid sample may have a composition according to the following general formula.

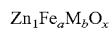

$$Zn_1Fe_aM_bO_x \qquad \text{General Formula 1}$$

In the general formula, a is from 2 to 2.8, b is from 0 to 0.2, and x may be determined by oxidation numbers of cations. In addition, as M, at least one may be selected from the group consisting of Be, Mg, Ca, Sr, Ba, Al, Cr, Co, Mn, Cu, Ni, La, Ce, Mo, Bi, P and Si.

According to one embodiment of the present specification, the heat treatment may be heat treating at 100° C. to 400° C.

According to one embodiment of the present specification, in the preparing of slurry by mixing the heat treated solid sample with distilled water and grinding the result, the grinding is not particularly limited as long as it is grinding the solid sample into fine particles, but may be carried out by ball milling. In addition, the solid content in the solid sample included in the slurry may be from 1% by weight to 30% by weight.

According to one embodiment of the present specification, in the loading of the ground solid sample into a carrier, the size and the shape of the carrier may vary depending on the size of a reactor to use in the reaction, and although not particularly limited thereto, the carrier may be ball or cylindrical with a diameter of 2 mm to 20 mm.

The loading refers to going through a process of inserting the ground solid sample into pores of the carrier, and may mean the ground solid sample being safely settled in pores of the carrier as well as adhering to a surface area of the carrier.

In addition, a rate of the oxidative dehydrogenation reaction of butene may be controlled by controlling the amount of the ferrite component per unit volume through the loading, and as a result, the heat of reaction may be effectively controlled.

The loading may be carried out by mixing the porous carrier and the slurry, and then drying the result while stirring, or by impregnating the amount of the slurry corresponding to a pore of the carrier, and then drying the result. The method of drying is not particularly limited, but may use a rotary evaporator. In addition, the process described above may be repeated several times in order to increase the loading amount of the solid component.

According to one embodiment of the present specification, the carrier may have a pore structure. The carrier is not particularly limited as long as it is a carrier having a pore structure, but may have pores with sizes capable of accommodating the ground solid sample into the pores of the carrier.

In addition, according to one embodiment of the present specification, the carrier may have a pore structure in which a pore size is from 10 um to 300 um and porosity is from 10% to 50% with respect to a total volume of the carrier.

As a method of measuring the pore size of the carrier, commonly usable techniques may be used, and the method is not particularly limited, however, mercury porosimeter may be used.

In addition, according to one embodiment of the present specification, the pore structure of the carrier allows the carrier to have a specific surface area of 0.005 $m^2/g$ to 0.5 $m^2/g$.

The specific surface area of the carrier concerns a loading property of the solid sample and performance as a catalyst, and when the specific surface area is smaller than 0.005 $m^2/g$, the reaction-occurring surface is not sufficiently provided making it difficult to expect target reaction performance, and when the specific surface area is larger than 0.5 $m^2/g$, it is difficult to make the pore size of the carrier large making it difficult to load the solid sample, and the role as a catalyst may not be fulfilled since the reactant is difficult to enter into the pores or the product is difficult to escape the pores. The surface area of the carrier may commonly be a BET surface area by $N_2$ adsorption.

According to one embodiment of the present specification, the carrier may be any one selected from the group consisting of alumina, silica, alumina/silica, silicon carbide, titania and zirconia. Specifically, alumina/silica may be included, and since this has a pore structure capable of stably loading the ferrite component into the carrier and has less acidic sites causing side reactions and thereby does not react with the ferrite component, chemical stability may be obtained.

According to one embodiment of the present specification, the baking of the slurry-loaded carrier may be carried out at 500° C. to 800° C. after vacuum drying or oven drying. The baking may mean enabling the ferrite component loaded into the pore of carrier to change into an active phase. When baking at a temperature lower than 500° C., the loaded ferrite component may not form an active phase reducing activity for the oxidative dehydrogenation reaction of butene, and when baking at a temperature higher than 800° C., a surface area of the active phase of the loaded ferrite component excessively decreases reducing activity for the oxidative dehydrogenation reaction of butene, and the ferrite component and the carrier may react and form a different crystalline phase reducing selectivity. Specifically, the baking may be carried out at 600° C. to 700° C.

One embodiment of the present specification may provide a ferrite catalyst for preparing butadiene prepared according to one embodiment of the present specification. The ferrite catalyst for preparing butadiene according to one embodiment of the present specification may prepare butadiene using a C4 mixture without further separation such as butane separation as a reactant.

According to one embodiment of the present specification, in the ferrite catalyst, the baked solid sample may be in 1% by weight to 30% by weight with respect to 100% by weight of the ferrite catalyst.

One embodiment of the present specification may provide a method for preparing butadiene using a ferrite catalyst including providing a gas mixture of oxygen, nitrogen, butene and steam; an oxidative dehydrogenation reaction performed by the gas mixture continuously passing through a catalyst layer fixing the catalyst according to one embodiment of the present specification; and yielding butadiene.

The butene may be a C4 mixture, and the type is not particularly limited as long as it is a C4 mixture, but may be selected from the group consisting of 1-butene, 2-butene, and C4 raffinate-1, 2, 2.5, 3.

A reactor used in the oxidative dehydrogenation reaction is illustrated in FIG. 1. The solid catalyst prepared according to one embodiment of the present specification is fixed in a straight molten salt type reactor, and the reactor is installed inside an electric furnace to circulate the molten salt and to steadily maintain an external temperature of a catalyst layer, and then the reaction proceeds while the reactant continuously passes through the catalyst bed in the reactor.

The temperature of the molten salt for progressing the oxidative dehydrogenation reaction may be from 250° C. to 550° C., specifically from 280° C. to 500° C., and more specifically may maintain a temperature of 300° C. to 450° C., and as for the injection amount of the reactant, the catalyst amount may be set to have a gas hourly space velocity (GHSV) of 50 $h^{-1}$ to 500 $h^{-1}$ based on butene.

According to one embodiment of the present specification, a method for preparing butadiene using a ferrite catalyst in which a molar ratio of the butene and the steam in the gas mixture is from 1:3 to 1:10 may be provided. When the molar ratio of the butene and the steam corresponds to the above-mentioned range, superior performance may be obtained in terms of explosion possibility, excellence of compression/cooling processes at a back end of the reactor, and minimization of heat loss. More specifically, a molar ratio of the butene, the oxygen, the nitrogen and the steam may be 1:0.5 to 1.5:0 to 10:3 to 10.

In the present specification, the butene, the oxygen and the nitrogen, reactants of the oxidative dehydrogenation reaction, are accurately controlled and supplied using a mass flow controller, and the steam may be injected after injecting water using a HPLC pump and then vaporizing the water. The butene, the oxygen and the nitrogen are mixed with the vaporized steam to be injected to the reactor. The temperature of an inlet part (front of heat exchange layer) is maintained at 150° C. to 300° C., and the gas mixture passes through the catalyst layer after going through the heat exchange layer.

Hereinafter, the present application will be more specifically described with reference to examples according to one embodiment of the present specification, however, the scope of the present disclosure is not limited thereto.

Catalyst Preparation 200 g of distilled water, 13.63 g of $ZnCl_2$ and 54.06 g of $FeCl_3.6H_2O$ were placed in a 500 ml beaker at room temperature, and then dissolved while stirring (aqueous precursor solution A). An aqueous NaOH solution having a concentration of 3 N was introduced to the aqueous precursor solution A, and precipitated until pH reached 9. After further stirring the result for 1 hour, the precipitates were separated using a vacuum filter, and washed several times with sufficient distilled water. The obtained solid sample (precipitates) was heat treated for 24 hours at 200° C. The heat treated solid sample was dispersed again into an aqueous solution and ball milled to prepare slurry, and a solid content of the prepared slurry was adjusted to be in a 5% by weight to 20% by weight range. Porous alumina/silica and the solid sample slurry were introduced and loaded using a rotary evaporator, and then heat treated for 5 hours under air atmosphere at 650° C. to prepare an oxidative dehydrogenation catalyst of butene including a zinc ferrite component. The content of the zinc ferrite component was adjusted to be in a 1% by weight to 30% by weight range.

Example 1

An oxidative dehydrogenation reaction of butene was performed using a catalyst loading 6.7% by weight of zinc ferrite into globular porous alumina/silica (SA5218, manufactured by Saint Gobain) having a diameter of 3 mm. The reaction was progressed in a tube reactor having an outer diameter of ½ inches and heated (or heat-controlled) by a molten salt. A sectional diagram of the reactor is illustrated in FIG. 1. After filling the reactor with 8 ml of the catalyst, flow rates of 2-butene (trans 60%, cis 40%), $O_2$ and $N_2$ were controlled using a mass flow controller, and a flow rate of steam was controlled using a HPLC pump so as to flow in a molar ratio of 2-butene/$O_2$/$N_2$/$H_2O$=1/0.75/2.82/5. The gas hourly space velocity (GHSV) was 125 $hr^{-1}$ based on 2-butene. The product at the reactor outlet was analyzed using GC.

Example 2

An oxidative dehydrogenation reaction of butene was performed using a catalyst loading 14.5% by weight of zinc ferrite into globular porous alumina/silica (SA5205, manufactured by Saint Gobain) having a diameter of 3 mm. The reaction condition was the same as in Example 1.

Example 3

An oxidative dehydrogenation reaction of butene was performed using a catalyst loading 11.5% by weight of zinc ferrite into globular porous alumina/silica (SA5205, manufactured by Saint Gobain) having a diameter of 5 mm. The reaction was progressed in a tube reactor having an outer diameter of ¾ inches and heated (or heat-controlled) by a molten salt. After filling the reactor with 20 ml of the catalyst, 2-butene/$O_2$/$N_2$/$H_2O$ were adjusted to flow in a molar ratio of 1/0.9/2.82/5. The gas hourly space velocity (GHSV) was 100 $hr^{-1}$ based on 2-butene.

Example 4

An oxidative dehydrogenation reaction of butene was performed using a catalyst loading 17.1% by weight of zinc ferrite into globular porous alumina/silica (SA5205, manufactured by Saint Gobain) having a diameter of 3 mm. The reaction condition was the same as in Example 1, and the gas hourly space velocity (GHSV) was 250 $hr^{-1}$ based on 2-butene.

Example 5

An oxidative dehydrogenation reaction of butene was performed using a catalyst loading 2.2% by weight of zinc ferrite into cylinder-shaped porous alumina/silica (SA5151, manufactured by Saint Gobain) having a diameter of 3 mm. The reaction condition was the same as in Example 1.

Example 6

An oxidative dehydrogenation reaction of butene was performed using a catalyst loading 3.7% by weight of zinc ferrite into globular porous silicon carbide (SC5232, manufactured by Saint Gobain) having a diameter of 3 mm. The reaction condition was the same as in Example 1.

Example 7

A catalyst was prepared adding $MgCl_2.6H_2O$ in the above-mentioned catalyst preparation step. 200 g of distilled water, 13.63 g of $ZnCl_2$, 2.03 g of $MgCl_2.6H_2O$ and 54.06 g of $FeCl_3.6H_2O$ were placed in a 500 ml beaker at room temperature, and then dissolved while stirring (aqueous precursor solution A). An aqueous NaOH solution having a concentration of 3 N was introduced to the aqueous precursor solution A, and precipitated until pH reached 9. After further stirring the result for 1 hour, the precipitates were separated using a vacuum filter, and washed several times with sufficient distilled water. The obtained solid sample (precipitates) was heat treated for 24 hours at 200° C. The heat treated solid sample was dispersed again into distilled water and ball milled to prepare slurry having a solid content of 10.0% by weight. Globular porous alumina/silica (SA5205) having a diameter of 3 mm and the catalyst slurry were introduced and loaded using a rotary evaporator, and then heat treated for 5 hours under 650° C. air atmosphere to prepare an oxidative dehydrogenation catalyst of butene including 11.8% by weight of a zinc ferrite component. After filling a ½ inch molten salt type reactor with 8 ml of the catalyst, flow rates of 2-butene (trans 60%, cis 40%), $O_2$, $N_2$ and steam were controlled so as to flow in a molar ratio of 2-butene/$O_2$/$N_2$/$H_2O$=1/0.75/2.82/5. The gas hourly space velocity (GHSV) was 400 $hr^{-1}$ based on 2-butene.

Example 8

A catalyst was prepared adding $AlCl_3.6H_2O$ in the above-mentioned catalyst preparation step. 200 g of distilled water, 13.63 g of $ZnCl_2$, 10.1 g of $MgCl_2.6H_2O$, 2.41 g of $AlCl_3.6H_2O$ and 54.06 g of $FeCl_3.6H_2O$ were placed in a 500 ml beaker at room temperature, and then dissolved while stirring (aqueous precursor solution A). An aqueous NaOH solution having a concentration of 3 N was introduced to the aqueous precursor solution A, and precipitated until pH reached 9. After further stirring the result for 1 hour, the precipitates were separated using a vacuum filter, and washed several times with sufficient distilled water. The obtained solid sample (precipitates) was heat treated for 24 hours at 200° C. The heat treated solid sample was dispersed again into distilled water and ball milled to prepare slurry having a solid content of 12.0% by weight. Globular porous alumina/silica (SA5205) having a diameter of 3 mm and the catalyst slurry were introduced and loaded using a rotary evaporator, and then heat treated for 5 hours under 650° C. air atmosphere to prepare an oxidative dehydrogenation catalyst of butene loading 11.5% by weight of a ferrite component. After filling a ½ inch molten salt type reactor with 8 ml of the catalyst, flow rates of 2-butene (trans 60%, cis 40%), $O_2$, $N_2$ and steam were controlled so as to flow in a molar ratio of 2-butene/$O_2$/$N_2$/$H_2O$=1/0.75/2.82/5. The gas hourly space velocity (GHSV) was 250 $hr^{-1}$ based on 2-butene.

Comparative Example 1

In the catalyst preparation step, 20 g of slurry having a solid content of 10% by weight and 50 g of non-porous globular alumina having a diameter of 3 mm were introduced, and the result was dried while mixing in a rotary evaporator. Subsequently, the result was heat treated for 3 hours at 650° C. to prepare a zinc ferrite-coated alumina catalyst. In the coating process and the heat treatment process, the zinc ferrite coated on the non-porous alumina was coated only in approximately 1.0% by weight to yield 50.02 g, and most of the zinc ferrite (99.0%) was not coated on the non-porous alumina or came off during a yielding process. After filling the reactor with 8 ml of the catalyst, an oxidative dehydrogenation reaction of butene was performed under the same reaction condition as in Example 1.

Comparative Example 2

Prior to the heat treatment in the catalyst preparation step, 5 g of the dried zinc ferrite, 50 g of boehmite, 30 g of distilled water and 1.5 g of nitrate (60%) were mixed, then 50 g of non-porous globular alumina having a diameter of 3 mm was introduced thereto, and the result was dried while mixing in a rotary evaporator. Subsequently, the result was heat treated for 3 hours at 650° C. to prepare a zinc ferrite-coated alumina catalyst. In the coating process and the heat treatment process, the zinc ferrite and the boehmite coated on the non-porous alumina were coated only in approximately 1.8% by weight to yield 50.99 g, and most of the zinc ferrite and the boehmite (approximately 98.2%) were not coated on the non-porous alumina or came off during a yielding process. After filling the reactor with 8 ml of the catalyst, an oxidative dehydrogenation reaction of butene was performed under the same reaction condition as in Example 1.

Comparative Example 3

Prior to the heat treatment in the catalyst preparation step, 5 g of the dried zinc ferrite, 50 g of boehmite, 30 g of distilled water and 3.0 g of nitric acid (60%) were mixed, then 50 g of non-porous globular silicon carbide having a diameter of 3 mm was introduced thereto, and the result was dried while mixing in a rotary evaporator. Subsequently, the result was heat treated for 3 hours at 650° C. to prepare a zinc ferrite-coated silicon carbide catalyst. In the coating process and the heat treatment process, the zinc ferrite and the boehmite coated on the non-porous silicon carbide were coated only in approximately 1.2% by weight to yield 50.66 g, and most of the zinc ferrite and the boehmite (approximately 98.8%) were not coated on the non-porous silicon carbide or came off during a yielding process. After filling the reactor with 8 ml of the catalyst, an oxidative dehydrogenation reaction of butene was performed under the same reaction condition as in Example 1.

Comparative Example 4

2000 g of distilled water, 136.3 g of $ZnCl_2$ and 540.6 g of $FeCl_3.6H_2O$ were placed in a 5000 ml beaker at room temperature, and then dissolved while stirring (aqueous precursor solution A). An aqueous NaOH solution having a concentration of 3 N was introduced to the aqueous precursor solution A, and precipitated until pH reached 9. After further stirring the result for 1 hour, the precipitates were separated using a vacuum filter, and washed several times with sufficient distilled water. The obtained solid sample (precipitates) was heat treated for 24 hours at 200° C., and then ground, kneaded by being mixed with water, and extruded to be formed into a cylinder shape having a diameter of 3 mm and a length of 3 mm, and the result was heat treated for 5 hours under 650° C. air atmosphere to prepare a pellet type zinc ferrite butene oxidative dehydrogenation catalyst. After filling the reactor with 8 ml of the catalyst, an oxidative dehydrogenation reaction of butene was performed under the same reaction condition as in Example 1.

Hereinafter, the experimental results are shown in Table 1.

TABLE 1

| | Reaction Temperature, ° C. (Molten Salt Temperature) | GHSV, $hr^{-1}$ | Butene/$O_2$/$N_2$/$H_2O$ | Conversion Rate (mol %) | Selectivity (mol %) |
|---|---|---|---|---|---|
| Example 1 | 359 | 125 | 1/0.75/2.82/5 | 85.1 | 93.3 |
| Example 2 | 342 | 125 | 1/0.75/2.82/5 | 86.5 | 93.7 |
| Example 3 | 356 | 100 | 1/0.90/2.82/5 | 93.4 | 92 |
| Example 4 | 352 | 250 | 1/0.75/2.82/5 | 84.9 | 93.3 |
| Example 5 | 379 | 125 | 1/0.75/2.82/5 | 82.4 | 92.8 |
| Example 6 | 371 | 125 | 1/0.75/2.82/5 | 83 | 93 |
| Example 7 | 403 | 400 | 1/0.75/2.82/5 | 83.2 | 93 |
| Example 8 | 348 | 250 | 1/0.75/2.82/5 | 85 | 93.4 |
| Comparative Example 1 | 394 | 125 | 1/0.75/2.82/5 | 63.6 | 88.1 |
| Comparative Example 2 | 397 | 125 | 1/0.75/2.82/5 | 55.4 | 84.9 |
| Comparative Example 3 | 406 | 125 | 1/0.75/2.82/5 | 53.1 | 83.9 |
| Comparative Example 4 | 311 | 125 | 1/0.75/2.82/5 | 38.5 | 72.4 |

When referring to Table 1, it was identified that, when using the ferrite catalyst according to one embodiment of the present specification, the conversion rate and the butadiene selectivity were enhanced compared to the catalyst formed into a pellet shape (Comparative Example 4) and the catalysts coated on a non-porous carrier surface (Comparative Examples 1 to 3). Process efficiency may be enhanced therethrough.

Example 9

200 g of distilled water, 13.63 g of $Zn(NO_3)_2 6H_2O$ and 54.06 g of $Fe(NO_3)_3 9H_2O$ were placed in a 500 ml beaker at room temperature, and then dissolved while stirring (aqueous precursor solution A). An aqueous $NH_4OH$ solution having a concentration of 3 N was introduced to the aqueous precursor solution A, and precipitated until pH reached 9. After further stirring the result for 1 hour, the precipitates were separated using a vacuum filter, and washed several times with sufficient distilled water. The obtained solid sample (precipitates) was heat treated for 24 hours at 200° C. The heat treated solid sample was dispersed again into distilled water and ball milled to prepare slurry. Porous alumina/silica (SA5218, manufactured by Saint Gobain) having a diameter of 3 mm and the slurry were introduced and loaded using a rotary evaporator, and then heat treated for 5 hours under 650° C. air atmosphere to prepare an oxidative dehydrogenation catalyst of butene including 6.5% by weight of a zinc ferrite component. The oxidative dehydrogenation reaction of butene was performed using the same reactor and under the same reaction condition as in Example 1.

Comparative Example—Preparation of MoBi-Based Catalyst 326.9 g of ammonium molybdate tetrahydrate ((NH$_4$)$_6$Mo$_7$O$_{24}$.4H$_2$O) was dissolved in 1300 g of distilled water (solution A). 320.8 g of cobalt nitrate (Co(NO$_3$)$_2$.6H$_2$O), 125.9 g of iron nitrate (Fe(NO$_3$)$_3$.9H$_2$O) and 18.0 g of cesium nitrate (CsNO$_3$) were dissolved in 250 g of distilled water (solution B). Separate from this, 75.6 g of bismuth nitrate (Bi(NO$_3$)$_2$.5H$_2$O) and 22.7 g of nitric acid were dissolved in 100 g of distilled water, and the result was introduced to the solution B to prepare an acidic solution having a cobalt, iron, bismuth and cesium precursor dissolved therein (solution C). The solution C was introduced in drops to the stirring solution A to prepare slurry.

Comparative Example 5

The prepared slurry was stirred for 1 hour at room temperature, and then dried for 24 hours at 120° C. to obtain a solid sample. The solid sample was ground, then kneaded by being mixed with water, and extruded to be formed into a cylinder shape having a diameter of 3 mm and a length of 3 mm, and the result was baked while maintaining air atmosphere at 450° C. to prepare a catalyst having a composition of Mo$_{12}$Bi$_1$Fe$_2$Co$_7$Cs$_{0.6}$O$_x$. An oxidative dehydrogenation reaction of butene was performed using the same reactor and under the same reaction condition as in Example 1.

Comparative Example 6

After impregnating the prepared slurry into globular porous alumina/silica (SA5205, manufactured by Saint Gobain) having a diameter of 3 mm, drying and baking processes were repeated to prepare a catalyst loading 17.4% by weight of a Mo$_{12}$Bi$_1$Fe$_2$Co$_7$Cs$_{0.6}$O$_x$ component. An oxidative dehydrogenation reaction of butene was performed using the same reactor and under the same reaction condition as in Example 1.

Comparative Example 7

The prepared slurry was stirred for 1 hour at room temperature, then dried for 24 hours at 120° C., and then heat treated at 300° C. Subsequently, the heat treated and dried solid sample was dispersed again into an aqueous solution, and then ball milled to prepare slurry, and a solid content of the prepared slurry was adjusted to be in a 5% by weight to 20% by weight range. After impregnating the result into globular porous alumina/silica (SA5205, manufactured by Saint Gobain) having a diameter of 3 mm, drying and baking processes were repeated to prepare a catalyst loading 18.1% by weight a Mo$_{12}$Bi$_1$Fe Co$_7$Cs$_{0.6}$O$_x$ component. An oxidative dehydrogenation reaction of butene was performed using the same reactor and under the same reaction condition as in Example 1.

The reaction results and changes in the catalyst component weight decrement after reacting for 100 hours are shown in the following Table 2.

TABLE 2

| | Reaction Temperature (° C.) (Molten Salt Temperature) | Conversion Rate/ Selectivity at 1 hr (%) | Conversion Rate/ Selectivity at 100 hr (%) | Catalyst Component Weight Decrement after 100 hr (%) |
| --- | --- | --- | --- | --- |
| Example 9 | 350 | 82.4/92.9 | 82.1/92.9 | 0.1 or less |
| Comparative Example 5 | 332 | 76.5/88.2 | 76.6/88.2 | 5.1 |
| Comparative Example 6 | 336 | 60.8/87.8 | 60.2/87.8 | 11.8 |
| Comparative Example 7 | 339 | 58.5/85.4 | 55.2/85.3 | 35.2 |

From Table 2, it was seen that Comparative Examples 5 to 7 using the catalyst preparation method of one embodiment of the present specification to a Mo—Bi-based catalyst had a relatively considerably decreased conversion rate after 100 hours compared to the ferrite catalyst using the catalyst preparation method of one embodiment of the present specification, and the catalyst component weight decrement was relatively high as well leading to a problem in durability.

The invention claimed is:

1. A method for preparing a ferrite catalyst comprising:
preparing an aqueous precursor solution including a metal precursor;
mixing the aqueous precursor solution with a basic solution and coprecipitating the result;
obtaining a solid sample through heat treatment after the coprecipitating;
preparing a slurry by mixing the solid sample in distilled water and grinding the result, wherein the slurry comprises 1% to 30% by weight of the solid sample;
loading the slurry into a carrier; and
baking the slurry-loaded carrier,
wherein the carrier has a pore structure in which pores have a pore size from 10 μm to 300 μm and porosity is from 10% to 50% with respect to a total volume of the carrier; and
wherein the carrier is any one selected from: silica, alumina/silica, silicon carbide, titania or zirconia.

2. The method for preparing a ferrite catalyst of claim 1, wherein the metal precursor includes any selected from: a metal nitrate precursor or a metal chloride precursor.

3. The method for preparing a ferrite catalyst of claim 2, wherein the metal nitrate precursor comprises zinc nitrate (Zn(NO$_3$)$_2$.6H$_2$O), iron nitrate (Fe(NO$_3$)$_3$.9H$_2$O) or a nitrate salt additive, and
the nitrate salt is any one or more selected from: beryllium nitrate (Be(NO$_3$)$_2$), magnesium nitrate (Mg(NO$_3$)$_2$.6H$_2$O), calcium nitrate (Ca(NO$_3$)$_2$.4H$_2$O), strontium nitrate (Sr(NO$_3$)$_2$.4H$_2$O), barium nitrate (Ba(NO$_3$)$_2$), aluminum nitrate (Al(NO$_3$)$_3$.9H$_2$O), chromium nitrate (Cr(NO$_3$)$_3$.9H$_2$O), cobalt nitrate (Co(NO$_3$)$_2$.6H$_2$O), manganese nitrate (Mn(NO$_3$)$_2$.6H$_2$O), copper nitrate (Cu(NO$_3$)$_2$.6H$_2$O), nickel nitrate (Ni(NO$_3$)$_2$.6H$_2$O), lanthanum nitrate (La(NO$_3$)$_3$.6H$_2$O), cerium nitrate (Ce(NO$_3$)$_3$.6H$_2$O) or bismuth nitrate (Bi(NO$_3$)$_3$.5H$_2$O).

4. The method for preparing a ferrite catalyst of claim 2, wherein the metal chloride precursor comprises zinc chloride (ZnCl$_2$), iron chloride (FeCl$_3$.6H$_2$O) and a chloride additive, and the chloride additive is any one or more selected from: beryllium chloride (BeCl$_2$), magnesium chloride (MgCl$_2$.6H$_2$O), calcium chloride (CaCl$_2$.6H$_2$O), strontium chloride (SrCl$_2$.6H$_2$O), barium chloride (BaCl$_2$.2H$_2$O), aluminum chloride (AlCl$_3$.6H$_2$O), chromium chloride (CrCl$_3$.6H$_2$O), cobalt chloride (CoCl$_2$.6H$_2$O), manganese chloride (MnCl$_2$.4H$_2$O), copper chloride (CuCl$_2$.2H$_2$O), nickel chloride (NiCl$_2$.6H$_2$O), lanthanum chloride (LaCl$_3$.7H$_2$O), cerium chloride (CeCl$_3$.7H$_2$O) or bismuth chloride (BiCl$_3$.5H$_2$O).

5. The method for preparing a ferrite catalyst of claim 1, wherein the basic solution is any one selected from: sodium hydroxide (NaOH), potassium hydroxide (KOH) or ammonium hydroxide (NH$_4$OH).

6. The method for preparing a ferrite catalyst of claim 1, wherein the coprecipitated solution has a pH of 5 to 10.

7. The method for preparing a ferrite catalyst of claim 1, wherein the coprecipitating is coprecipitating while mixing the aqueous precursor solution with a basic solution having a molar concentration of 1.5 to 12 at 10° C. to 40° C.

8. The method for preparing a ferrite catalyst of claim 1, wherein the ferrite catalyst includes a carrier and a baked solid sample, and the baked solid sample has a composition according to the following General Formula 1:

$$Zn_1Fe_aM_bO_x \qquad \text{General Formula 1}$$

in General Formula 1,
a is from 2 to 2.8;
b is from 0 to 0.2;
x is determined by oxidation numbers of cations; and
M is at least one is selected from: Be, Mg, Ca, Sr, Ba, Al, Cr, Co, Mn, Cu, Ni, La, Ce, Mo, Bi, P or Si as M.

9. The method for preparing a ferrite catalyst of claim 1, wherein the heat treatment is heat treating at 100° C. to 400° C.

10. The method for preparing a ferrite catalyst of claim 1, wherein the grinding is by ball milling.

11. The method for preparing a ferrite catalyst of claim 1, wherein the carrier is globular or cylindrical having a diameter of 2 mm to 20 mm.

12. The method for preparing a ferrite catalyst of claim 1, wherein a pore structure of the carrier allows the carrier to have a specific surface area of 0.005 m$^2$/g to 0.5 m$^2$/g.

13. The method for preparing a ferritic catalyst of claim 1, wherein the baking is carried out at 500° C. to 800° C. after vacuum drying or oven drying the slurry-loaded carrier.

14. A ferrite catalyst for preparing butadiene prepared using the method of claim 1.

15. The ferrite catalyst for preparing butadiene of claim 14, wherein, in the ferrite catalyst, the baked solid sample is in 1% by weight to 30% by weight with respect to 100% by weight of the ferrite catalyst.

16. A method for preparing butadiene using a ferrite catalyst comprising:

providing a gas mixture of oxygen, nitrogen, butene and steam;

an oxidative dehydrogenation reaction performed by the gas mixture continuously passing through a catalyst layer fixing the catalyst prepared using the method of claim 1; and yielding butadiene.

17. The method for preparing butadiene using a ferrite catalyst of claim 16, wherein a molar ratio of the butene and the steam in the gas mixture is from 1:3 to 1:10.

* * * * *